United States Patent [19]
Robinson

[11] Patent Number: 6,036,459
[45] Date of Patent: Mar. 14, 2000

[54] OCCLUSION COMPENSATOR FOR IMPLANTABLE PERISTALTIC PUMP

[75] Inventor: Reginald D. Robinson, Plymouth, Minn.

[73] Assignee: Medtronic, Inc., Minneapolis, Minn.

[21] Appl. No.: 09/004,208

[22] Filed: Jan. 8, 1998

Related U.S. Application Data

[63] Continuation-in-part of application No. 08/627,985, Apr. 4, 1996, Pat. No. 5,840,069.

[51] Int. Cl.$^7$ ........................................... F04B 43/12
[52] U.S. Cl. ................................ 417/477.7; 417/477.8; 417/477.11
[58] Field of Search ......................... 417/477.5, 477.7, 417/477.8, 477.11

[56] References Cited

U.S. PATENT DOCUMENTS

| | | | |
|---|---|---|---|
| 862,867 | 8/1907 | Eggleston | 417/472 |
| 3,549,279 | 12/1970 | Grach | 417/477.7 |
| 3,822,948 | 7/1974 | Handl | 417/477.7 |
| 3,838,977 | 10/1974 | Warren | 23/288 |
| 4,576,556 | 3/1986 | Thompson | . |
| 4,692,147 | 9/1987 | Duggan | . |

FOREIGN PATENT DOCUMENTS

| | | | |
|---|---|---|---|
| 2452771 | 5/1976 | Germany | 417/477.7 |

*Primary Examiner*—Charles G. Freay
*Assistant Examiner*—Cheryl J. Tyler
*Attorney, Agent, or Firm*—Banner & Witcoff, Ltd.

[57] ABSTRACT

A peristaltic pump which may be used as an implantable medical device includes a rotor arm that is provided with a means for applying a regulated occluding force to the pump rollers. In a preferred embodiment, an expandable chamber containing a pressurized material may be incorporated into the pump. In this manner the pressure within the expandable chamber and thus the force applied to the pump roller may be kept constant despite local variations in the dimensions of the components and associated variations in the volume of the expandable chamber. Alternatively, the pressure within the expandable chamber may be modulated by the pressure of a reservoir communicating with the pump inlet or modulated by pump operating parameters such as motor torque.

33 Claims, 8 Drawing Sheets

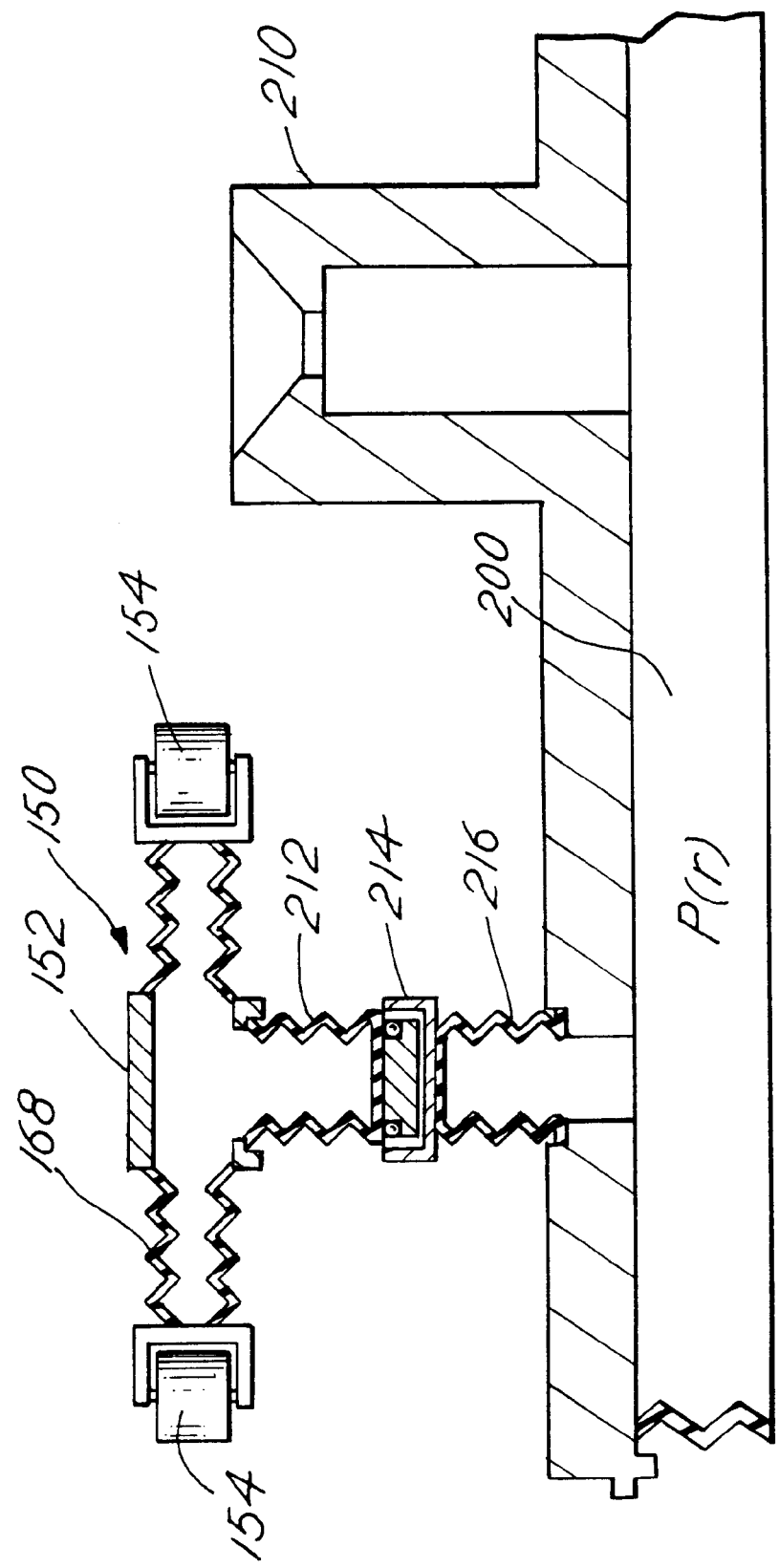

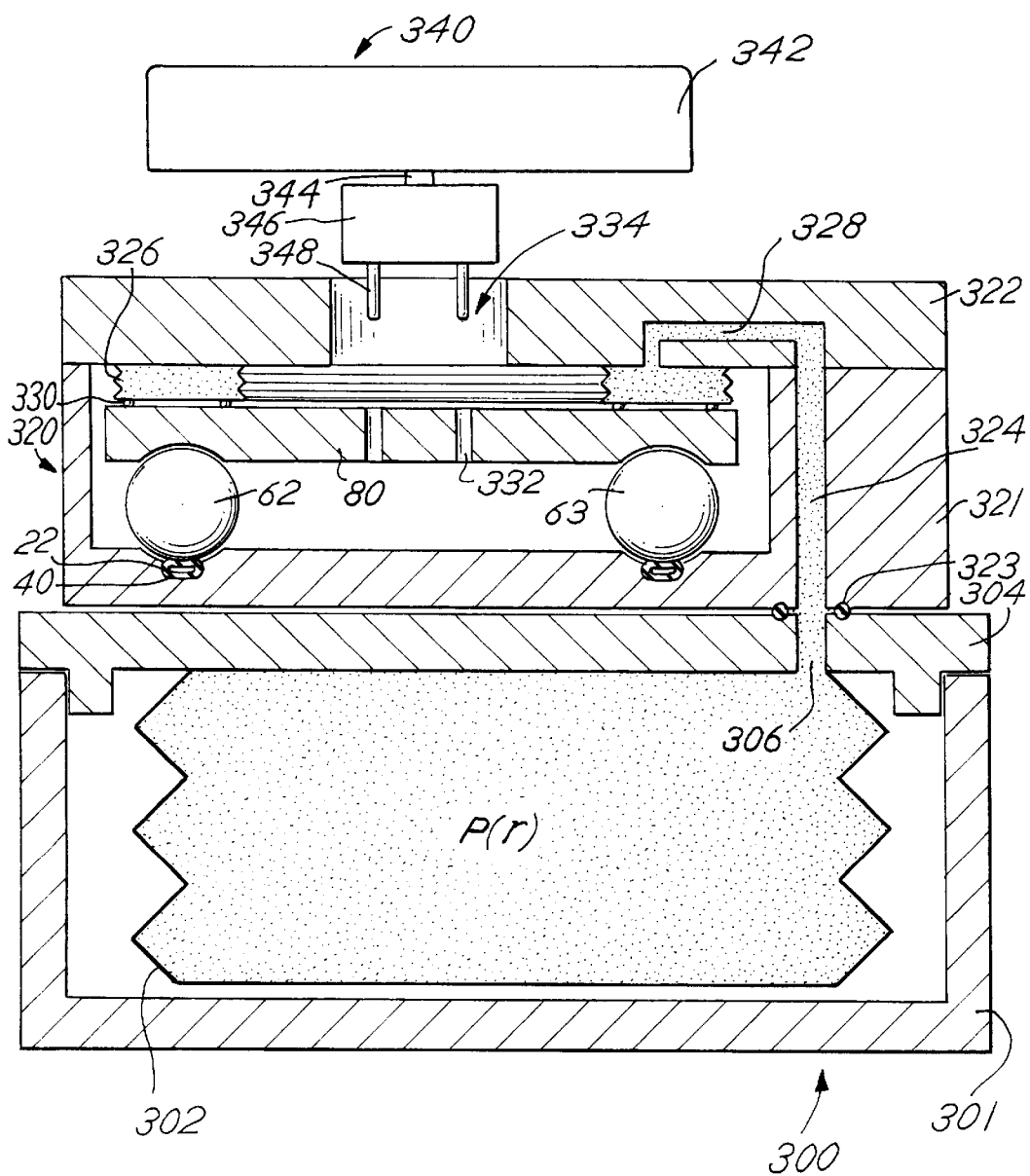

OCCLUSION COMPENSATOR FOR IMPLANTABLE PERISTALTIC PUMP

This is a continuation in part of copending U.S. patent application Ser. No. 08/627,985 filed Apr. 4, 1996.

BACKGROUND OF THE INVENTION

This invention relates in general to peristaltic pumps and more particularly to implantable peristaltic pumps for infusing treatments into an organism.

Peristaltic pumps find general application in the medical field. They operate on the principle that a flexible tube provided with advancing occluded portions, usually caused by rotating rollers held against the tube periphery, can be used to pump fluid from one location to another. These pumps incorporate coplanar geometry in which the pump rollers orbit within the plane defined by the pump tube, which is held in a stationary race. Peristaltic pumps that are exemplary of the prior art are disclosed in U.S. Pat. No. 4,692,147 (Duggan) and U.S. Pat. No. 4,576,556 (Thompson), both assigned to Medtronic, Inc. of Minneapolis, Minn. The subject matter of these patents is incorporated herein by reference.

One problem associated with the prior art pumps is that they typically require a great deal of effort and expense in their assembly and maintenance in order to closely control the tolerances relating to the tube alignment and the occluding force applied by the rollers to various portions of the tube. For example, Duggan, while providing a highly accurate peristaltic pump, requires close tolerances and accurate machining of some pump components, which adds considerably to manufacturing expense. The pump tube described by Duggan is extruded with flanges or wings protruding from the outer wall of the tube. These features help insure that the pump tube remains aligned in a race. However, the presence of the flange increases costs by complicating the tube fabrication process. The pump race requires additional depth to accommodate the wings and adds to the inherent thickness of the pump assembly. The pump described by Duggan requires an alignment procedure that has proven to be time consuming and expensive.

Another problem with prior art pumps involves the control of the occlusion force applied to the pump tube. Often, a pressurized reservoir is provided in communication with the pump tube inlet to facilitate the advance of the pumped fluid. It is desirable to provide sufficient occluding force on the pump tube to prevent reservoir-pressure induced leakage through the occluded portion of the pump tube, which might be catastrophic. Frequently, prior art pumps are assembled in a significantly over-occluded state to ensure sufficient occlusion forces at all points on the pump tube. On the other hand, over-occlusion—excessive compressive load on the tube—is undesirable because it results in unnecessary friction and leads to increased wear and excessive power consumption by the pump drive system. Excessive power consumption is particularly undesirable in the field of implantable, battery-powered pumps. Over-occlusion results in increased cyclic loading of the pump tube and thus reduces the tube leakage safety margin and useful life. Similarly, over-occlusion results in unnecessary wear on the pump rollers, bearings and other components. In the past, much time and effort has been expended to address these competing factors.

The level of occluding force needed to prevent leakage past the occluded portion of the tube is a function, in part, of the inlet pressure on the pump tube. In implantable pumps, a pressurized reservoir is provided in fluid communication with the pump tube to supply treatment to the pump inlet. The reservoir is charged with a propellant as well as the treatment. As the reservoir is emptied, pressure will decrease and the amount of occluding force necessary to prevent leakage through the occluded portions of the pump tube is reduced. Theoretically, then, the torque and therefore the power required to operate the pump rotor could be reduced as the pump inlet pressure decreases. Prior art pumps, however, have provided no means to take advantage of this principle, leading to unnecessary expenditure of pump power and over occlusion of the pump tube.

It is known to provide pump tubes with shims at various locations on the tube periphery to control the occluding force. Shims may take the form of a silicone rubber sheet that is fit between the rollers and the tube. Shims are provided in varying thicknesses, depending on the gap between the pump roller surfaces and the pump race at varying points along the race. Shims are selectively matched to various parts of the pump tube to compensate for variances in tube, pump housing and race dimensions and to achieve the optimum occlusion force at all points on the pump tube. Each individual pump has to be inspected and measured to determine the proper shim thicknesses to be applied at appropriate points along the tube. This has resulted the expenditure of considerable time and effort in pump manufacturing in the past.

It is also known, as exemplified in the implantable device of Thompson, to provide spring-biased rollers on the pump rotor in order to provide a resilient force outward against the tube. Such a passive spring configuration, however, has only a limited ability to control the occluding force applied to the pump tube.

SUMMARY OF THE INVENTION

According to a preferred embodiment, a pump tube holds liquid to be pumped, and the tube defines an axis lying along a path. A first race supports the tube in a first plane. Roller means compress the tube at one or more points along the path in a direction non-parallel to the first plane. Means are provided for moving the roller means relative to the tube along the path so that liquid is moved through the tube. By using the foregoing arrangement, a highly accurate peristaltic pump can be fabricated with low tolerances. No machining is required, and the pump parts are easily assembled.

In accordance with another aspect of the invention there is provided a peristaltic pump with a rotor that includes a means for regulating the occluding force applied to the tube. In a preferred embodiment, the means for regulating takes the form of an expansible chamber defined on the rotor and containing a fluid-vapor phase material to provide a constant or controlled pressure within the chamber. The chamber may communicate with the pump reservoir such that the occluding force may be regulated in response to changes in reservoir pressure.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 7A–7C are cross-sections of a rotor according to a preferred embodiment of the present invention; and FIG. 8 is a cross-section of a pump according to another preferred embodiment of the present invention wherein the occluding force is modulated by reservoir pressure.

FIG. 9 is a cross-section of a pump according to another preferred embodiment of the invention wherein a means for regulating the occluding force is incorporated into a stratified pump geometry.

DESCRIPTION OF THE PREFERRED EMBODIMENTS

Figure 1:
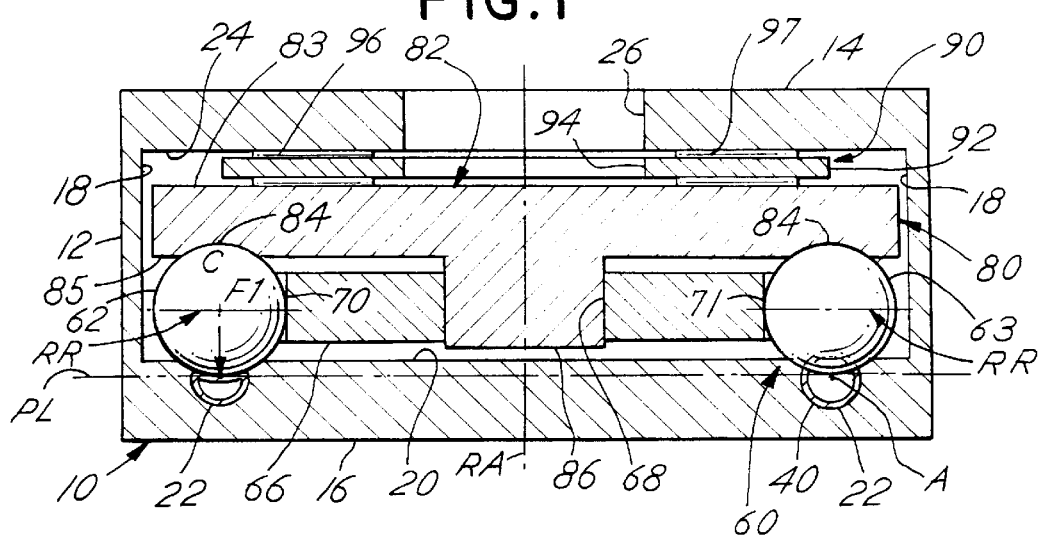
FIG. 1 is a cross-section, taken along line 1—1 of FIG. 2, of a preferred form of pump made in accordance with the present invention.
Figure 2:
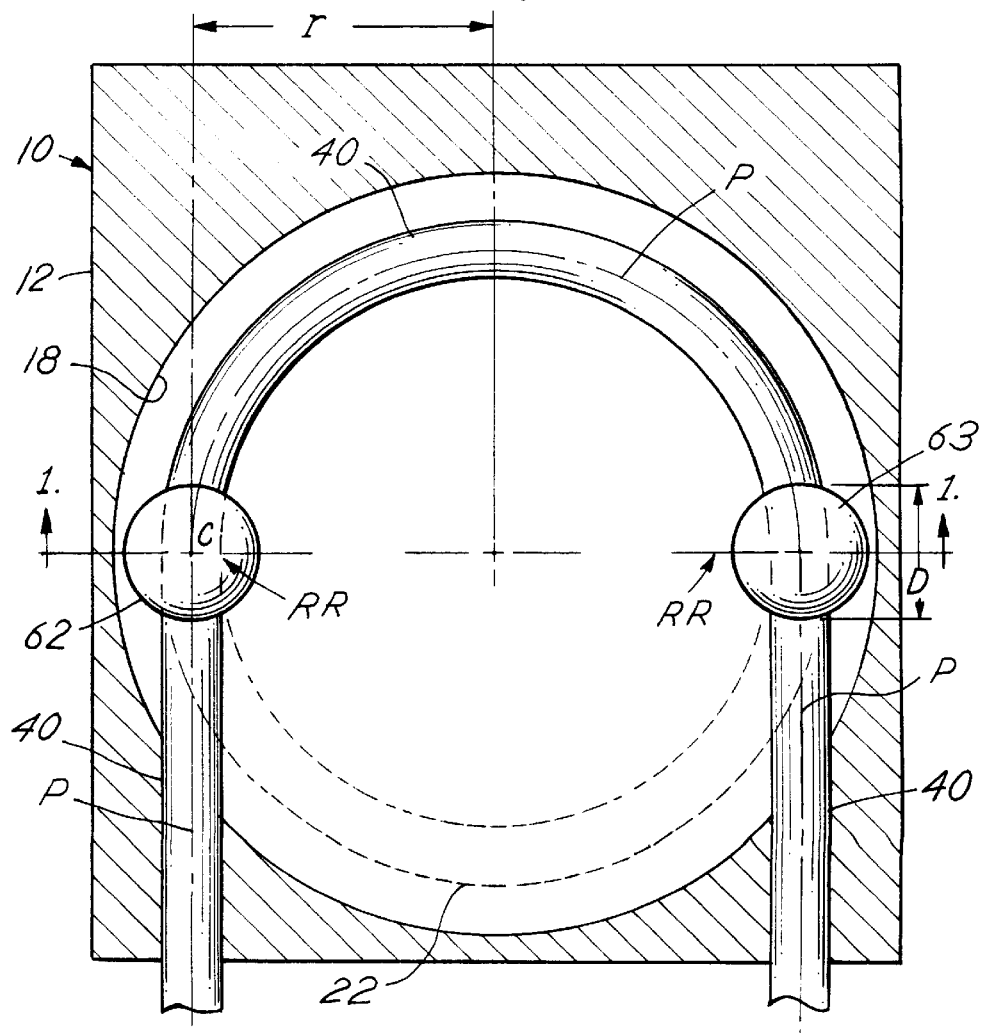
FIG. 2 is a top plan view of the pump shown in FIG. 1 with the top portion of the housing and the roller assembly removed to reveal the inner parts.

Referring to FIGS. 1 and 2, FIG. 1 being a cross-section taken along line 1—1 of FIG. 2, a preferred form of peristaltic pump made in accordance with the present invention comprises a housing 10, a peristaltic pump tube 40, a roller assembly 60, a drive assembly 80, and a bearing assembly 90.

Housing 10 comprises an outer surface 12, a top surface 14 and a bottom surface 16. Housing 10 defines a cylindrical inner wall 18, as well as an inner bottom surface 20 that defines a circular race or depression 22. Housing 10 also includes an inner top surface 24 defining a central cylindrical opening 26 to allow the entry of a drive mechanism to turn the pump. The housing can be broken into top and bottom segments (not shown) for ease of assembly.

Peristaltic pump tube 40 is a flexible tube having an inner diameter of 0.040 inch, an outer diameter of 0.060 inch and preferably is fabricated from silicone rubber. Tube 40 has a cylindrical cross-section that defines an axis A and extends through a path P. As shown in FIG. 1, axis A lies in a plane PL. Tube 40 is supported by surface 20 in depression 22.

Figure 3:
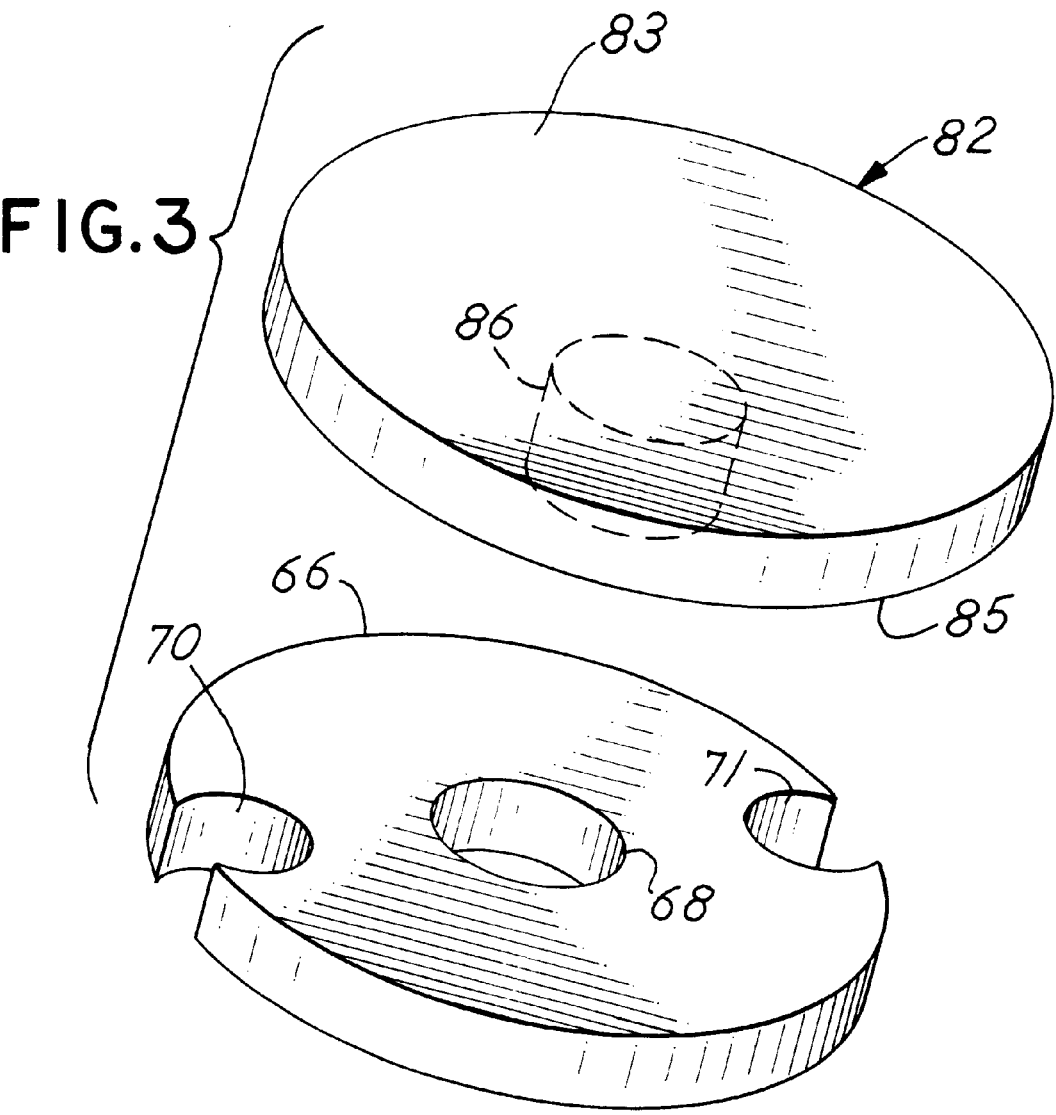
FIG. 3 is a perspective view of two of the parts shown in FIG. 1.

Roller assembly 60 comprises rollers 62 and 63 that are conventional, spherical ball-bearings. Assembly 60 also includes a spacer 66 fabricated from PTFE. Spacer 66 defines a central opening 68 and includes cylindrical cut out portions 70 and 71 that contain and guide rollers 62 and 63 (FIG. 3).

Drive assembly 80 includes a disk 82 having a top surface 83 and a bottom surface 85 that forms a circular roller race 84 adapted to comate with rollers 62 and 63. Integrally formed with disk 82 is a depending collar 86 that fits into and rotates within opening 68 of spacer 66 (FIGS. 1 and 3). Disk 82 rotates around an axis RA in order to drive rollers 62 and 63 around axis RA.

As shown in FIG. 1, rollers 62 and 63 exert an occlusion force, such as F1, perpendicular to plane PL in order to compress tube 40 in the manner shown in the left-hand portion of FIG. 1. Tube 40 is shown in phantom in the right-hand portion of FIG. 1 in its uncompressed state for purposes of comparison with the compressed state. However, roller 63 in fact compresses tube 40 as shown under arrow F1. Having force F1 applied to tube 40 in a non-parallel direction relative to plane PL offers a distinct advantage which allows for ease of assembly.

Bearing assembly 90 comprises a conventional roller bearing 92 defining a central opening 94 and including a plurality of rollers, such as 96 and 97. A drive mechanism from a pump motor may be attached to the top surface of disk 82 through openings 26 and 94 (FIG. 1). The pump may be driven by the same motor described in the '147 patent.

Spacer 66 may accommodate two or more rollers depending on the type of motor used to drive the pump and the rate of liquid flow required from tube 40. Rather than using roller bearing 92, the top inner surface 24 of the housing and the top surface 83 of disk 82 can be made from low-friction material, like PTFE, thereby eliminating the necessity for a roller bearing or ball-bearing assembly.

In order to assemble the pump, tube 40 is bonded in the pump tube groove 22, and rollers 62 and 63 are placed in cut out portions 70 and 71 of spacer 66. Drive disk 82 is placed on top of the roller assembly and is coupled with a motor. As disk 82 turns around axis RA, the spacer 66 and rollers 62 and 63 rotate around axis RA approximately 0.5° for every 1.0° of disk 82 rotation. Fluid from a pressurized reservoir is pushed along inside tube 40 ahead of the advancing rollers in the manner of a conventional peristaltic pump. As rollers 62 and 63 advance along path P, they compress tube 40 as shown in the left-hand portion of FIG. 1, thereby moving liquid through the tube in the direction of travel of the rollers. Rollers 62 and 63 are advanced solely by friction from disk 82. This is an important feature which contributes to the ability of the pump to provide the precise operation without the necessity for machine parts or holding close tolerances.

As explained above, as disk 82 rotates about axis RA, spacer 66 and rollers 62 and 63 rotate around axis RA approximately 0.5° for every 1.0° of disk 82 rotation. It will be recognized that this geometry provides a mechanical reduction in the amount of rotation imparted to rollers 62 and 63 per unit rotation of disk 82. It will also be recognized that this configuration provides a multiplication of torque applied to rollers 62 and 63 compared to the torque applied to drive disk 82. The particular mechanical reduction achieved may be explained with reference to the radius of orbit (r), which is the distance from the rotational axis (RA) of drive assembly 80 to the point of contact Ⓒ of rollers 62 and 63. It will be recognized that, by appropriate selection of roller diameter (D) and radius of orbit (r), the amount of rotation imparted to rollers 62 and 63 per unit rotation of drive assembly 80 can be selected and a desired degree of pump flow per unit rotation of drive assembly 80 can be achieved. This aspect of the invention is advantageous not only in offering more precise control of the movement of rollers, but in eliminating the need for additional components in the motor and/or drive train to achieve mechanical travel reduction and torque multiplication.

Figure 4:
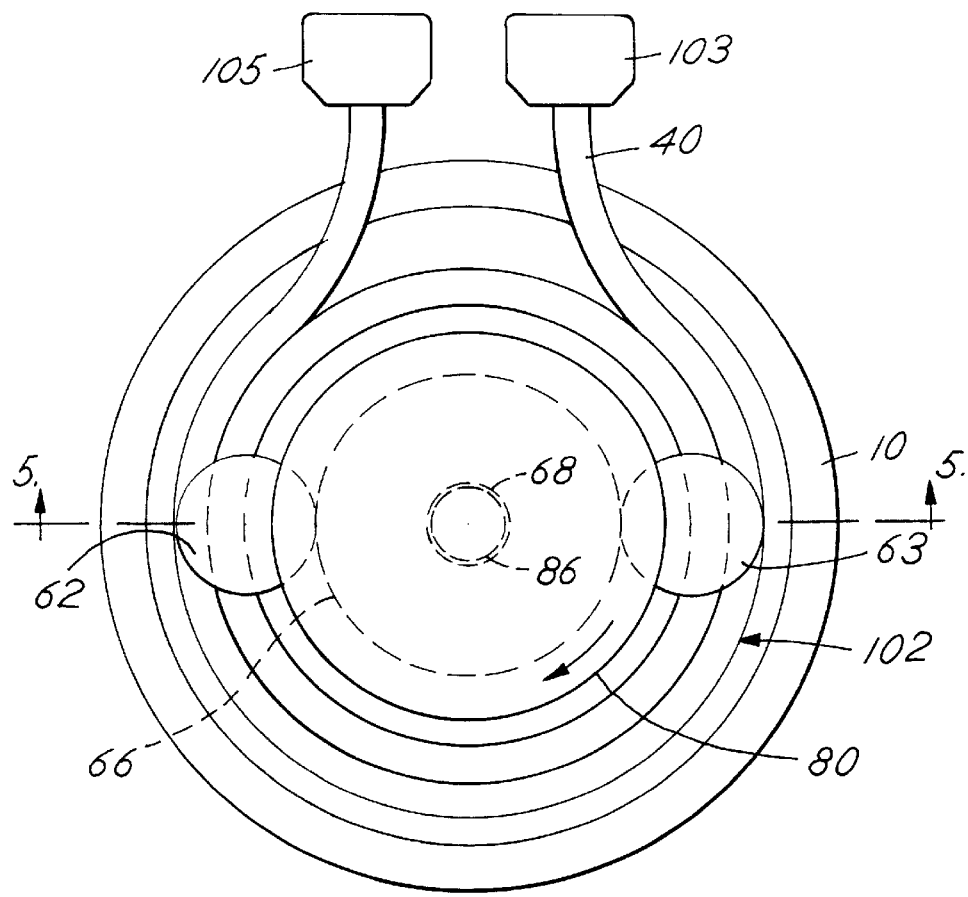
FIG. 4 is a top plan view of a pump according to another preferred embodiment of the invention.
Figure 5:
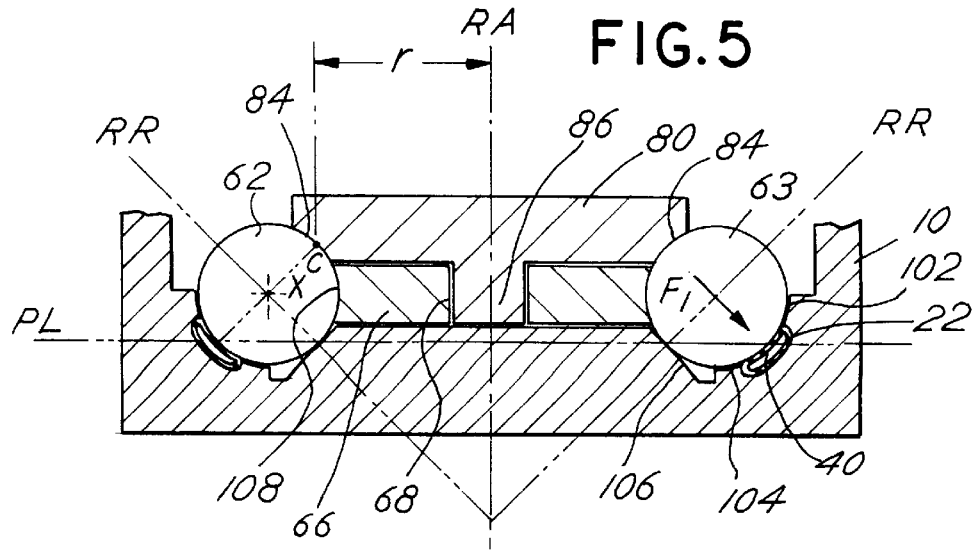
FIG. 5 is a cross-section taken along line 5—5 of FIG. 4.

Referring now to FIGS. 4 and 5, an alternative embodiment of the present invention incorporates a geometry in which the occluding forces are applied to the tube at an angle other than 90-degrees to the tube plane PL. Housing 10 includes a depression or race 22 formed therein for receiving pump tube 40 which communicates with a pump inlet 103 and a pump outlet 105. Rollers 62 and 63 are provided in the form of spherical balls, engaged by conical or angled drive surface 84 of drive disk 80. Drive disk 80 may be constructed of a resilient material which is suitable to provide sufficient frictional engagement of rollers 62 and 63. Drive surface 84 is shown as an arcuate surface, which may be provided in the undeformed drive disk 80 or which, alternatively, may result from deformation of a substantially square edge of drive disk 80. Housing 10 is provided with roller engaging surfaces 102 and 104 adjacent depression 22, which guide rollers 62 and 63. An additional roller guiding surface 106 may also be provided such that rollers 62 and 63 may be easily oriented within housing 10 during assembly. Driving surface 84 and guiding surfaces 102, 104 and 106 are preferably shaped complementarily to the arcuate surface of spherical rollers 62 and 63 to maximize the frictional contact therebetween and thereby provide for rolling motion and prevent sliding motion thereof. Spacer 66 may be comprised of a resilient material incorporating PTFE to reduce friction and is disposed between drive disk 80 and housing 1. Spacer 66 includes a central opening 68 for receiving depending collar 86, which may be an integral part of drive assembly 80. Spacer 66 may be provided with guiding surfaces 108 for engaging or guiding spherical rollers 62 and 63. Alternatively, spacer 66 may be provided with holes (not shown) similar to those in spacer 66 illustrated in FIGS. 1 and 2, such that spacer 66 surrounds rollers 62 and 63.

Drive disk 80 is connected to a motive means, such as a motor with suitable couplings (neither motor nor couplings is shown). Drive assembly 80 will thus exert an occluding force through driving surface 84 against rollers 62 and 63 and ultimately against pump tube 40 in the direction shown by arrow F1. Those of ordinary skill will recognize that the embodiment illustrated in FIGS. 4 and 5, in a manner similar to the embodiment illustrated in FIGS. 1 and 2, provides a mechanical reduction in the travel of rollers 62 and 63. In this case, the particular radius of orbit (r) is determined by defining roller contact point Ⓒ by a line perpendicular to roller rotational axis RR and drawn through the roller center (X).

Figure 6:
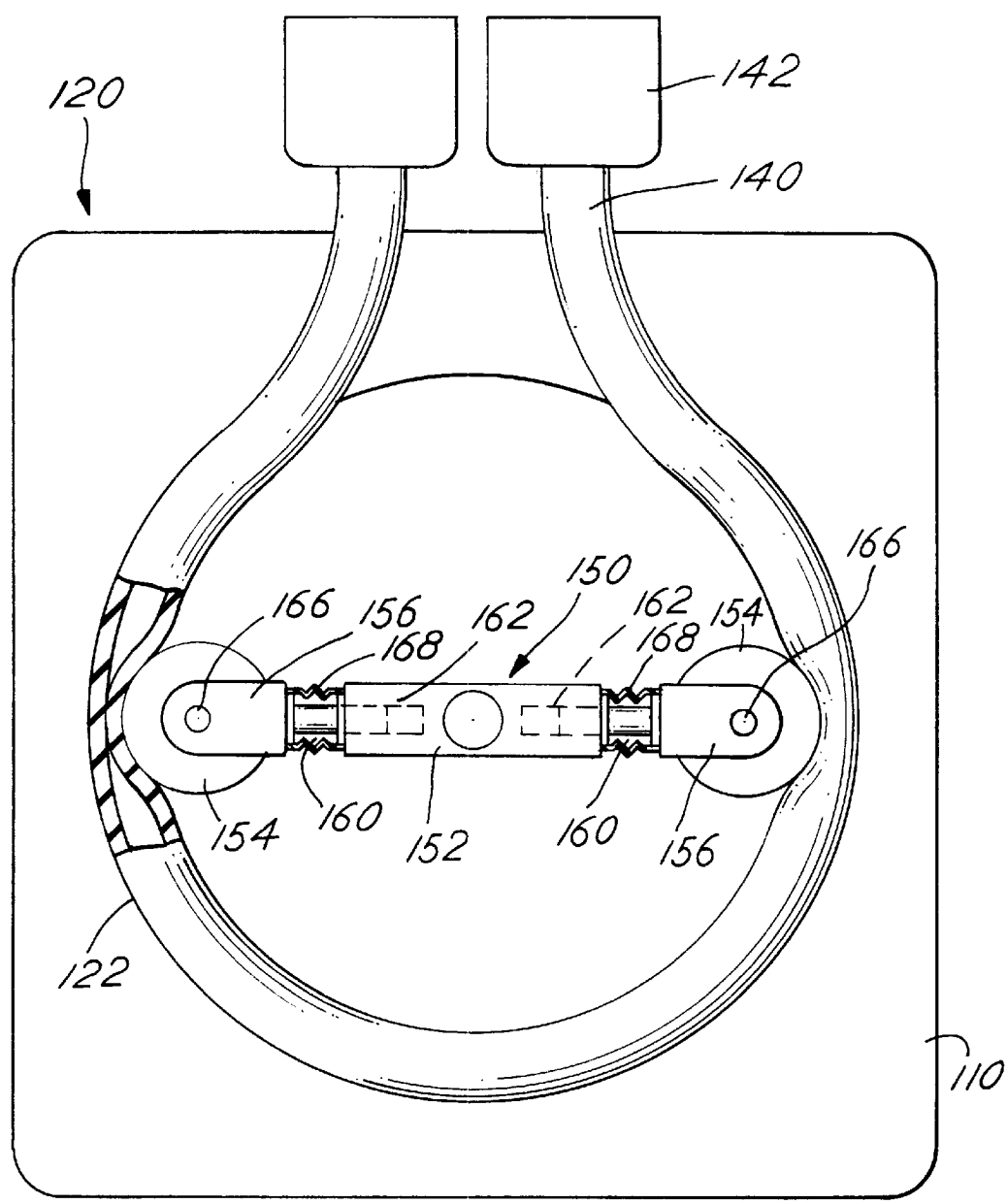
FIG. 6 is a top plan view of a preferred embodiment of a pump according to another aspect of the present invention.

FIGS. 6–7 illustrate a peristaltic pump according to another aspect of the present invention wherein the pump is provided with a drive assembly that is capable of applying a regulated occluding force to the rollers and pump tube. The occluding force may be kept substantially constant, or may be adjusted in response to changes in various operational parameters.

FIG. 6 is a plan view of a peristaltic pump 120 that has been modified in accordance with the present invention. Pump 120 is comprised of housing 110, pump tube 140 and drive assembly including a rotor 150. Housing 110 includes circular race 122 for supporting the pump tube 140. Pump tube 140 has an inlet end 142 which may communicate with a pressurized reservoir (not shown). Pump rotor 150 is rotatably mounted within housing 110 and includes a rigid arm 152 and two rollers 154 mounted at opposite ends of rotor 150 via yokes 156. Pump rotor 150, rollers 154 and race 122 are configured such that tube 140 is compressed between the outer surface of rollers 154 and the race 122 of pump housing 110 as shown in the cutaway.

Figures 7A, 7B, 7C:
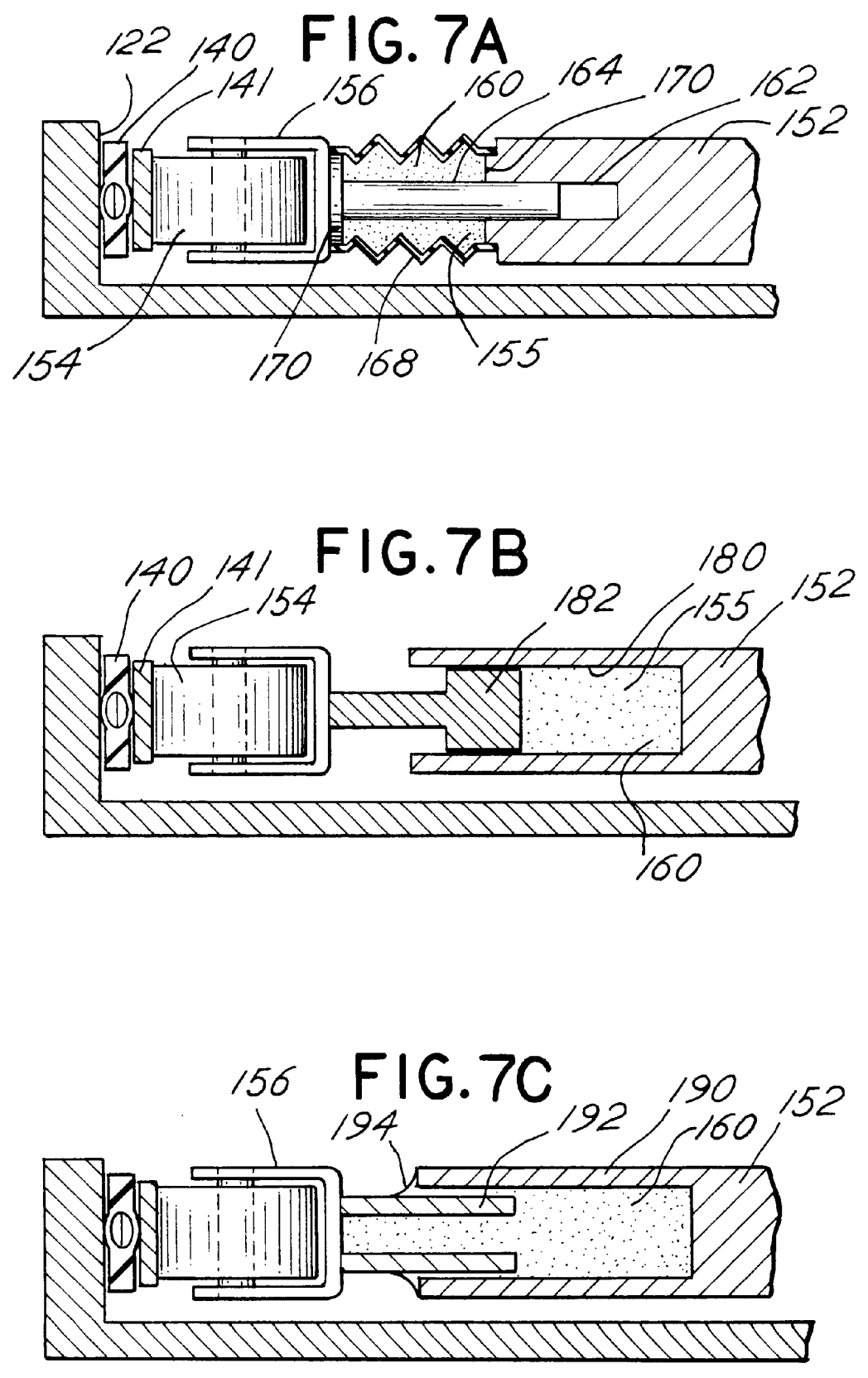

Referring to FIG. 7A in addition to FIG. 6, in accordance with the present invention, rotor 150 is provided with means for applying a regulated force to rollers 154 and pump tube 140, the means in this embodiment comprising a pair of expandable chambers 160 defined by bellows 168 and telescoping shafts 164. Shafts 164 are slidably received in journals 162 formed in rotor arm 152. The means for applying a regulated force also comprises a fluid 155 (represented by dots) contained in expandable chamber 160. The fluid may be either a liquid, vapor or mixture thereof, the pressure of which is regulated in order to achieve a regulated occluding force against the pump tube. Rotor 150 is coupled to the drive shaft of a motor (not shown). Journalled within yoke members 156 are pins 166 for rotably securing rollers 154 thereto. Bellows 168 may comprise any material suitable for permitting relative motion between telescoping shafts 164 and journals 162 while maintaining a sealed condition. Bellows 168 is sealed by suitable means, i.e. clamps, adhesive or the like, around collars 170 formed on rotor arm 152 and yoke members 156. In FIG. 7A, tube 140 includes lateral flanges extending parallel to race 122. A shim 141 (optional) is disposed adjacent tube 140 to mitigate wear. This particular configuration is useful for creating rather large reaction forces against the rollers 154 when tube side walls are compressed against one another.

If the occluding force is desired to be regulated by maintaining a constant force on rollers 154, chambers 160 may be provided with a liquid-vapor phase material, for example, a liquid-vapor phase propellant. Characteristic of such materials is the ability to maintain a constant pressure regardless of the volume occupied by the liquid and vapor phases of the material, which phases exist in equilibrium. When the volume of chambers 160 increases, due, for example, to variations in the tube, rotor, housing or shim dimensions through the rotation of rotor 150 some of the propellant in liquid form will evaporate into the vapor phase to maintain the pressure within chambers 160 at a constant value. Thus, the same occluding force will be exerted on the pump tube 140 despite variations in the linear extent of rotor 150. Propellant may be introduced into expansible chamber 160 via a sealed port (not shown) or other suitable means.

FIG. 7B illustrates an alternative embodiment for expandable chamber 160. Here, chamber 160 is defined by a cylinder 180 formed in rotor arm 152 and by a piston 182 slidably received in cylinder 180. Piston 182 is affixed to yoke member 156 to transmit the occluding force to rollers 154. Chamber 160 may be provided with a liquid-vapor phase material 155 as described above to provide a constant occluding force to tube 140 via shim 141.

FIG. 7C illustrates yet another alternative embodiment for expandable chamber 160. Here chamber 160 is defined by a cylinder 190 formed in rotor arm 152, another smaller cylinder 192 connected to yoke 156 and a diaphragm 194 affixed to both cylinder 190 and smaller cylinder 192. It will be understood that the dimensions of cylinder 190 and smaller cylinder 192 should be chosen such that sufficient lateral strength and support (in the direction of the rotor rotation) is provided. Alternatively, diaphragm 194 may be replaced by a hydraulic seal capable of permitting telescoping movement and maintaining a tight seal between smaller cylinder 192 and cylinder 190.

While the above embodiments reflected in FIGS. 6 and 7 have been described with reference to a constant occluding force, applicant has contemplated that the means for applying a regulated force to the pump tube may also act to maintain an occluding force that is modulated by, i.e., controlled in response to, pump operational parameters, which may include reservoir pressure and/or motor torque. With reference to FIG. 8, an embodiment is shown in which the occluding force is modulated by reservoir pressure. Reservoir 200 is incorporated into the pump body 210. Rotor 150 is formed with a pair of first bellows 168 in the manner disclosed with reference to FIGS. 6 and 7A. Rotor arm 152 is connected to a motive means (not shown). A second bellows 212 is provided in fluid communication with first bellows 168 and is supported on thrust bearing 214. Second bellows 212 and first bellows 168 define a volume which contains a first working fluid. A third bellows 216 is provided adjacent thrust bearing 214 to apply a force thereto. Third bellows 216 communicates with the interior of reservoir 200, which contains treatment and/or propellant at pressure P(r). Here, as reservoir pressure decreases, the occluding force applied by rollers 154 may be reduced without resulting in leakage past the occluded portions of tube 140. First, second and third bellows, together with thrust bearing 214 and the pressurized fluid in reservoir 200 thus provide a means for regulating the occluding force applied by rollers 154 in which occluding force is modulated by the reservoir pressure. The bellows lengths illustrated in FIG. 8 have been exaggerated for clarity. Typically, the bellows will be much more compact than illustrated such that the distance between the upper surface of pump body 210 and the upper surface of rotor 152 is on the order of one-half inch. As an alternative to bellows 168 of FIG. 8, the piston cylinder arrangement of FIG. 7B may be employed and may incorporate hydraulic amplifiers to cause a greater change in occluding force per unit change of reservoir pressure. Similarly, the diaphragm arrangement illustrated in FIG. 7C may be used.

FIG. 9 is a cross-section of another preferred embodiment of the present invention in which a means for regulating the occluding force is incorporated into a stratified pump geometry. The pump comprises three main components: reservoir housing 300, pump housing 320, and drive assembly 340. Reservoir housing 300 includes reservoir base assembly 301 which houses bellows 302. Bellows 302 contains propellant at a pressure P(r). Base 301 is provided with reservoir housing top 304, which includes port 306 that communicates with the interior of bellows 302. Assembly of the reservoir housing 300 proceed with ease as the bellows 302 is assembled into the interior of base 301 and then sealed with reservoir housing top 304. It should be noted that bellows assembly 302 is fastened and sealed to the inside surface of reservoir housing top 304 with suitable means (not shown). Reservoir housing top is sealed against base 301 with suitable sealant and fasteners (neither is shown).

Pump housing 320 includes pump base assembly 321 and pump housing top 322 which together provide an enclosed space that houses the pump components. The pump components illustrated in this embodiment are similar to those disclosed with respect to FIGS. 1–5. Like numerals have been used to refer to parts which are similar to or find counterparts in those figures. In accordance with one aspect of the present invention, a donut bellows 326 is provided as a means for regulating the occluding force of rollers 62 and 63 against pump tube 40. In FIG. 9, donut bellows 326 is shown in cross-section. It will be recognized that donut bellows 326 has a generally circular shape when viewed from a direction upward or downward and parallel to the plane of the Figure. The interior of bellows 326 communicates with the pressurized fluid in bellows 302 via first conduit 328 in the pump housing top of 322 and second conduit at 324 in the pump housing. Pump housing 320 is sealed against the top surface of reservoir housing top 304 using an "O" ring 323. Donut bellows 326 applies an occluding force against drive disk 80 via bearing elements 330 which are fastened to the bellows 326 in a known manner. Those of ordinary skill will recognize that suitable sealing means are provided such that the pressure within bellows 302 is communicated to the interior of donut bellows 326 without leakage. Pump housing top 322 is fastened to the top of pump housing 321 using known implements such that no leakage occurs past the interface between pump housing 321 and top 322. Donut bellows 326 provides a means for applying a regulated force to the pump tube 40 via rollers 62 and 63 in such a manner that the force is modulated by the pressure in the reservoir 302.

Drive assembly 340 comprises motor unit 342 and coupling 346 which is attached to the shaft 344 of the motor. Coupling 346 includes a pair of prongs 348 which engage complimentarily shaped recesses 332 in the drive assembly 80. This construction permits the assembly of the motor unit from a vertical direction in keeping with the stratified construction of the pump. Coupling 346 is received in opening 334 and are slidably received in recesses 332 such that driving force may be applied from motor 342 to drive disk 80 as the vertical position of drive disk 80 changes. Motor 342 is fastened to the pump housing top 322 using suitable fastening techniques.

Figure 10:
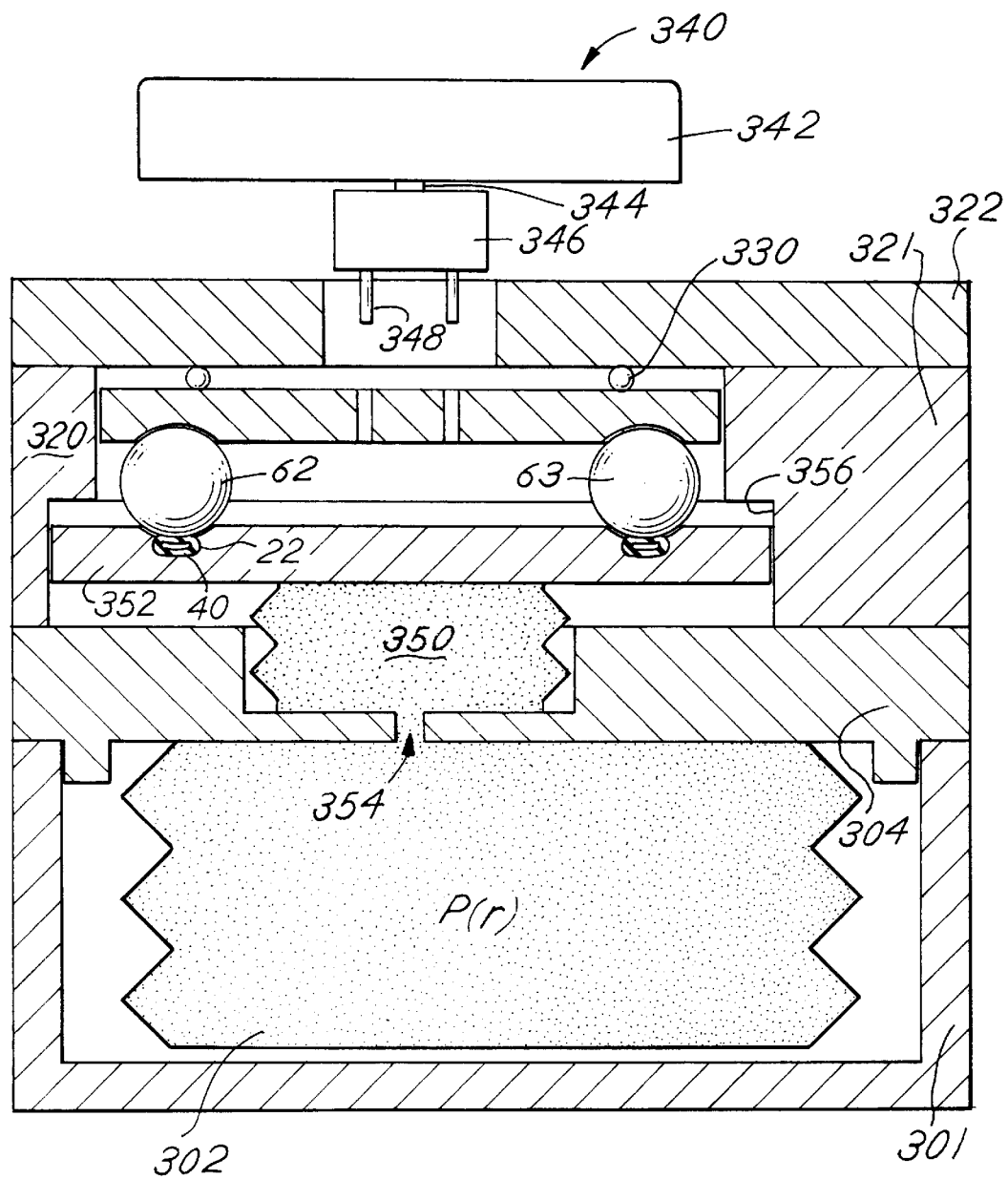
FIG. 10 is a cross-section of a pump according to another preferred embodiment of the present invention wherein a means for regulating the occluding force is incorporated into a stratified pump geometry.

FIG. 10 illustrates a cross-section of another preferred embodiment of the invention having stratified pump geometry. Elements finding response in FIG. 9 are referred to with like numerals. FIG. 10 illustrates an alternative construction having race 22 provided in a movable platform 352. Platform 352 is fastened to an elevating bellows 350, the interior volume of which communicates via port 354 with the interior volume of reservoir bellows 302. Platform 352 is preferably of a circular shape and journalled in a recess 356 formed in pump housing 321 to permit vertical movement with respect thereto. Bearing elements 330 are provided between the upper surface of drive disk 80 and the lower surface of pump housing top 322 to reduce friction therebetween. In this embodiment, rollers 62 and 63 remain substantially in the same vertical position while the occluding force on tube 40 is regulated by the force applied to platform 352 by elevating bellows 350.

Those skilled in the art will recognize that the preferred embodiments may be altered and modified without departing from the true spirit and scope of the invention as defined in the appended claims. For example, while modulation of the occluding force by reservoir pressure has been disclosed, it will be recognized that other operating parameters may be utilized to modulate the occluding force.

What is claimed is:

1. A peristaltic pump comprising:
   a flexible pump tube defining an inner volume for containing a fluid to be pumped;
   a race for supporting the pump tube;
   at least one roller for applying an occluding force to the tube;
   a drive assembly for advancing the at least one roller, the drive assembly including means for applying a regulated force to the at least one roller; and
   a pressurized reservoir external to and in direct communication with the means for applying the regulated force, the means for applying the force being modulated by pressure in the reservoir.

2. The pump according to claim 1, wherein the means for applying a regulated force comprises an expandable chamber disposed in the drive assembly.

3. The pump according to claim 2, wherein the means for applying a regulated force further comprises a vapor-liquid material contained in the expandable chamber for maintaining a constant pressure therein.

4. The pump according to claim 2, wherein the expandable chamber is defined by a piston and cylinder.

5. The pump according to claim 2, wherein the expandable chamber is defined at least in part by a bellows.

6. The pump according to claim 2, wherein the expandable chamber is defined at least in part by a diaphragm.

7. The pump according to claim 1, wherein the at least one roller is adapted to apply the occluding force to the tube in a direction non-parallel to a plane defined by the pump tube as supported in the race.

8. The pump according to claim 7, wherein the means for applying a regulated force to the at least one roller comprises a donut bellows adapted to apply a force to the drive assembly.

9. The pump according to claim 7, wherein the means for applying a regulated force to the at least one roller comprises a bellows adapted to apply a force to the race.

10. The pump according to claim 1, wherein the at least one roller is spherical.

11. A peristaltic pump comprising:
a flexible pump tube defining an inner volume for containing a fluid to be pumped;
a race for supporting the pump tube;
at least one roller for applying an occluding force to the tube;
a rotor for advancing the at least one roller along the pump tube;
means for applying a force to the at least one roller such that a regulated occluding force is applied to the pump tube; and a pressurized reservoir external to and in direct communication with the means for applying the regulated force, the means for applying a force being modulated by pressure in the reservoir.

12. The pump according to claim 11, wherein the means for applying a force comprises an expandable chamber disposed in the drive assembly.

13. The pump according to claim 11, wherein the means for applying a force is adapted to apply a constant occluding force to the pump tube.

14. The pump according to claim 13, wherein the means for applying a force comprises an expandable chamber defined in the rotor and containing a vapor-liquid material which acts to maintain a constant pressure in the chamber.

15. The pump according to claim 11, wherein the means for applying a force comprises an expandable chamber defined in the rotor, the pressure in the expandable chamber being modulated by the pressure in the reservoir.

16. The pump according to claim 15, wherein the expandable chamber is defined at least in part by a bellows.

17. The pump according to claim 15, wherein the expandable chamber is defined at least in part by a telescoping shaft.

18. The pump according to claim 15, wherein the expandable chamber is defined at least in part by a diaphragm.

19. The pump according to claim 11, wherein the at least one roller is adapted to apply the occluding force to the tube in a direction non-parallel to a plane defined by the pump tube as supported in the race.

20. The pump according to claim 11, wherein the means for applying a regulated force to the at least one roller comprises a donut bellows adapted to apply a force to the drive assembly.

21. The pump according to claim 11, wherein the means for applying a regulated force to the at least one roller comprises a bellows adapted to apply a force to the race.

22. The pump according to claim 11, wherein the at least one roller is spherical.

23. A peristaltic pump comprising:
a flexible pump tube defining an inner volume for containing a fluid to be pumped;
a race for supporting the pump tube;
at least one roller for applying an occluding force to the tube;
a drive assembly for advancing the at least one roller, the drive assembly being coupled to an expandable chamber that is in direct communication with a reservoir disposed external to the expandable chamber, the expandable chamber applying a force to the drive assembly modulated by pressure in the reservoir.

24. The pump according to claim 23, wherein the expandable chamber further comprises a vapor-liquid material contained in the expandable chamber for maintaining a constant pressure therein.

25. The pump according to claim 23, wherein the expandable chamber is defined by a piston and cylinder.

26. The pump according to claim 23, wherein the expandable chamber is defined at least in part by a bellows.

27. The pump according to claim 23, wherein the expandable chamber is defined at least in part by a diaphragm.

28. The pump according to claim 23, wherein the expandable chamber is defined at least in part by a first bellows.

29. The pump according to claim 28, wherein the expandable chamber is defined at least in part by a second bellows.

30. The pump according to claim 23, wherein the at least one roller is adapted to apply the occluding force to the tube in a direction non-parallel to a plane defined by the pump tube as supported in the race.

31. The pump according to claim 30, wherein the expandable chamber comprises a donut bellows adapted to apply a force to the drive assembly.

32. The pump according to claim 30, wherein the expandable chamber comprises a bellows adapted to apply a force to the race.

33. The pump according to claim 23, wherein the at least one roller is spherical.

* * * * *